United States Patent
Klein

(10) Patent No.: US 10,247,681 B2
(45) Date of Patent: Apr. 2, 2019

(54) MEASURING DEVICE FOR MEASURING THE DIELECTRIC AND / OR MAGNETIC PROPERTIES OF A SAMPLE BY MEANS OF A MICROWAVE TRANSMISSION MEASUREMENT, APPARATUS USING SUCH A MEASURING DEVICE, AND METHOD USING SUCH AN APPARATUS

(71) Applicant: Elisabeth Katz, Simmersfeld (DE)

(72) Inventor: Albert Klein, Simmersfeld (DE)

(73) Assignee: ELISABETH KATZ, Simmersfeld (DE)

( * ) Notice: Subject to any disclaimer, the term of this patent is extended or adjusted under 35 U.S.C. 154(b) by 0 days.

(21) Appl. No.: 15/749,738

(22) PCT Filed: Jul. 28, 2016

(86) PCT No.: PCT/EP2016/067999
§ 371 (c)(1),
(2) Date: Feb. 1, 2018

(87) PCT Pub. No.: WO2017/025340
PCT Pub. Date: Feb. 16, 2017

(65) Prior Publication Data
US 2018/0231476 A1     Aug. 16, 2018

(30) Foreign Application Priority Data
Aug. 7, 2015 (DE) .................. 10 2015 010 300

(51) Int. Cl.
*G01N 22/04*     (2006.01)
*G01N 22/00*     (2006.01)

(52) U.S. Cl.
CPC ............. *G01N 22/04* (2013.01); *G01N 22/00* (2013.01)

(58) Field of Classification Search
CPC ....... G01N 22/02; G01N 22/00; G01N 33/442
See application file for complete search history.

(56) References Cited

U.S. PATENT DOCUMENTS

| 5,838,158 A | 11/1998 | Beck et al. |
| 9,476,843 B2 | 10/2016 | Klein |

(Continued)

FOREIGN PATENT DOCUMENTS

| DE | 10 2012 010 255 B3 | 11/2013 |
| EP | 0 990 887 A2 | 4/2000 |
| KR | 10-2015-0081537 A | 7/2015 |

OTHER PUBLICATIONS

International Search Report (PCT/ISA/210) issued in PCT/EP2016/067999, dated Oct. 24, 2016.

*Primary Examiner* — Giovanni Astacio-Oquendo
*Assistant Examiner* — Alvaro Fortich
(74) *Attorney, Agent, or Firm* — Birch, Stewart, Kolasch & Birch, LLP

(57) ABSTRACT

A microwave measuring device having a transmitting module and a receiving module and an apparatus having these modules are described. The two modules are accommodated either in a common housing or in separate housings. The transmitting module can be coupled to a transmitting antenna and the receiving module can be coupled to a receiving antenna. In order to compensate for measurement errors, in particular temperature-related measurement errors, at least one RF bypass cable runs outside the housing/the housings and can be used to couple the transmitting module and the receiving module while bridging the measuring section defined by the two antennas.

20 Claims, 8 Drawing Sheets

(56) References Cited

U.S. PATENT DOCUMENTS

| | | | |
|---|---|---|---|
| 2004/0138838 A1* | 7/2004 | Scheiner | G01B 7/105 |
| | | | 702/64 |
| 2006/0164104 A1* | 7/2006 | Tada | G01B 15/02 |
| | | | 324/646 |
| 2014/0187930 A1* | 7/2014 | Hirabayashi | A61B 5/002 |
| | | | 600/430 |
| 2015/0091585 A1 | 4/2015 | Klein | |

* cited by examiner

MEASURING DEVICE FOR MEASURING THE DIELECTRIC AND / OR MAGNETIC PROPERTIES OF A SAMPLE BY MEANS OF A MICROWAVE TRANSMISSION MEASUREMENT, APPARATUS USING SUCH A MEASURING DEVICE, AND METHOD USING SUCH AN APPARATUS

The invention relates to a measuring device for measuring the dielectric and/or magnetic properties of a sample by means of a microwave transmission measurement according to the preamble of claim 1, an apparatus using such a measuring device according to claim 10 and a measuring method using such an apparatus.

In engineering various possibilities are known, of how the dielectric properties of a sample, for example moisture, can be measured without contact. For example, it is possible to irradiate the sample with microwaves and obtain the desired information by comparing the irradiated microwave, or a signal derived there from with the transmitted microwave, or a signal derived there from. Herewith, both the absorption as well as the phase shift can be determined so that the complete information about the complex epsilon of the sample can be obtained from the corresponding measurement. An apparatus suitable for this purpose comprises a transmitting module and a receiving module that are usually accommodated in a common housing made of metal. Herewith, the transmitting module has at least one radio frequency generator (usually called a synthesis generator, also called synthesizer) for generating a high frequency signal that is coupled into a HF coupling unit (transmitting antenna) connected to the synthesis generator, for which purpose a transmitting-side HF connecting cable is provided. The synthesis generator is clocked by a so-called frequency standard that outputs a low-frequency signal with a frequency, for example, of 10 MHz. The high-frequency signal generated by at least one synthesis generator is also fed to the receiving module that is connected to a HF decoupling unit (receiving antenna) and mixed there in a mixer with the microwave received by the receiving antenna. For connection between the HF decoupling unit and the receiving module a receiving-side HF connecting cable is provided. HF coupling unit (transmitting antenna) and HF decoupling unit (receiving antenna) define a measuring section in which a sample is arranged in a measuring operation. Furthermore, an evaluation unit is provided, which can be designed as a separate module. The mixed signal is fed to this evaluation unit.

One basically distinguishes between two types of measuring systems, namely the so-called homodyne systems that operate at one time with only one frequency and have only one high-frequency generator, and the so-called heterodyne systems that operate with two closely adjacent frequencies and have two synthesis generators. Both systems are equal in that they operate by comparing two microwave signals, one passing through the sample, thereby experiencing attenuation and/or phase shift, while the other microwave signal does not pass through the sample and serve as reference. This makes it necessary to provide a high frequency reference line (Lo line) between the transmitting module and the receiving module (this applies to both homodyne and heterodyne systems). In case the transmitting and receiving modules are accommodated in one housing, the high-frequency reference line may run inside the housing, in case the transmitting and receiving modules are housed in physically separate housing, a HF reference cable extending between the housing is provided, which forms a part of the HF reference line.

The measurement setup does not directly provide the input attenuation and phase shift of the sample, but rather the transfer function of the measurement system including the sample. Therefore, an empty measurement is additionally required, which provides the transfer function of the measuring system without the sample. Only the calculation of the two transfer functions provides the vector transfer function (S21) of the sample, i.e. attenuation and phase shift.

Under laboratory conditions, the provision of the above-mentioned high-frequency reference line is usually unproblematic, since on the one hand no large local distances must be overcome, and on the other hand constant laboratory conditions, in particular a substantially constant temperature prevail.

If such an apparatus is used in the industrial sector, the following problem arises: the temperature dependence of the wave propagation velocity in a coaxial cable comprising an increased effect on the phase shift as the frequency of the wave increases. This means that under non-constant environmental conditions, in particular temperatures, significant phase shifts in the antenna feed lines (transmitting side HF connecting cable and receiving side HF connecting cable) and, if present, in the HF reference cable can occur which falsify the measurement result. In industrial applications, however, it is often unavoidable that at least one of the HF cables is made relatively long (a few meters), which of course aggravates this problem, especially if such an apparatus is installed outdoors, so that it completely or partially exposed to the sunlight.

Furthermore, measurement inaccuracies may occur (again in industrial applications in particular) if strong reflections occur around the measurement section. In particular, in open measurement systems where the sample is in a free-space measurement section without contact, measurement errors occur due to reflections on the sample or are caused on reflectors in the surrounding.

In order to be able to achieve good measurement results consistently even under fluctuating environmental conditions, DE 10 2012 010 255 B3 proposes to provide at least one synthesis generator for generating a high-frequency signal both on the transmitting side and on the receiving side and to couple these two synthesis generators in a phase-stable and reproducible manner, for which purpose a common frequency standard is provided, which activates the two synthesis generators via at least one low-frequency signal line, which is referred to here as a low-frequency synchronisation signal line. The provision of a receiving-side synthesis generator makes the use of the above-mentioned problematic high-frequency reference line superfluous in many applications, so that even if the transmitting module and the receiving module are spatially separated from each other, no temperature-sensitive high-frequency reference cable is necessary. Due to the fact that transmitting module and receiving module are separated locally, the possibility is created to keep the antenna cables relatively short. Only a low-frequency line (in the form of a low-frequency cable) of great length may be provided if necessary, which connects the two modules to one another. Such low-frequency signal lines are almost insensitive to the above-mentioned environmental influences even at great length, so that no recalibration is necessary even under strongly fluctuating environmental influences, in particular a strongly changing temperature. Such an apparatus can be designed both as a homodyne system and as a heterodyne system.

The proposed system works well in principle, but it has the disadvantage that it works ideally only if it is operated permanently at a constant frequency or at two constant frequencies. However, working with multiple frequencies can be problematic, especially if a frequency band is "run through" if the synthesis generators must change their frequencies at certain intervals. Since the locally spaced synthesis generators are coupled by a common low-frequency signal whose frequency is typically lower by a factor of 100 to 500 than the frequency of the synthesis generators, it cannot be ensured that the two synthesis generators "lock in" on the same wave flank, which in turn can lead to inconsistent phase errors.

The object of the invention based on this is to provide an improved measuring device or device for measuring the dielectric and/or magnetic properties of a sample by means of a microwave transmitting measurement.

This object is met by a measuring device with the features of claim 1 and by an apparatus having the features of claim 9.

According to the invention, at least one HF bypass signal line is provided in the measuring operation, the input of which can be coupled into the signal path between the first HF synthesis generator and the HF coupling unit and whose output can be coupled into the signal path between the HF coupling unit and the mixer, so that when the bypass signal line is coupled in, the HF signal is redirected from the measurement section to the first HF bypass signal line. Part of this HF bypass signal line is formed as HF bypass cable extending outside the housing/the housings.

This means that one can switch over between the measuring section and the HF bypass signal line during the measuring operation, so that the first input of the mixer can be fed with either the HF signal that has passed through the measuring section, or with the HF signal that has bypassed the measuring section via the at least one HF bypass signal line, so that in addition to the measurements on the sample also calibration measurements can be performed. Due to the possibility of calibration measurements, the following improvements can be achieved:

In a first embodiment of the invention, the provision of an HF bypass cable serves to compensate for measurement errors caused by temperature changes in the HF connecting cables to the antennas. For this purpose, the HF bypass cable is preferably designed such that it comprises the same thermal and electrical properties as the HF connecting cables to the antennas and that its length comprises the total length of the HF connecting cable. Hereby, the HF bypass cable is preferably laid such that it has the same temperature as the HF connecting cable. If a second HF bypass cable with a different length is used additionally, the measurement error caused by a drift of the electronics can be compensated.

In a second embodiment in which the device is designed according to the principle described in DE 10 2012 010 255 B3, the calibration measurement is used for the purpose such that when changing the frequency, the error caused by different "snapping in place" of synthesis generators is mathematically compensated (that is by the evaluation unit).

In order not to "deal with" errors again due to fluctuating environmental conditions, such as, in particular, fluctuating temperatures, it is also preferable in this case to provide two HF bypass signal lines which differ in length, wherein the two HF bypass signal lines have the same electrical and thermal properties, wherein HF bypass signal line can be switched over between the two, so that the possibility of a double calibration measurement is created.

Finally, the calibration measurement can serve to eliminate the influence of interfering reflections in the case of an empty measurement. So far, an empty measurement is made as a comparison measurement when the measurement section is empty, so that the influence of the sample on the microwave that passes through it can be determined by subtraction. However, the disturbing reflections occur primarily when the measuring section is empty. Therefore, this measurement is replaced by the calibration measurement that is a bypass measurement. In addition, then in a second measurement, the difference of the transfer function of the empty measurement section in relation to the HF bypass signal line must be determined, from which then the average value of the attenuation and phase shift is determined.

Figure 1:
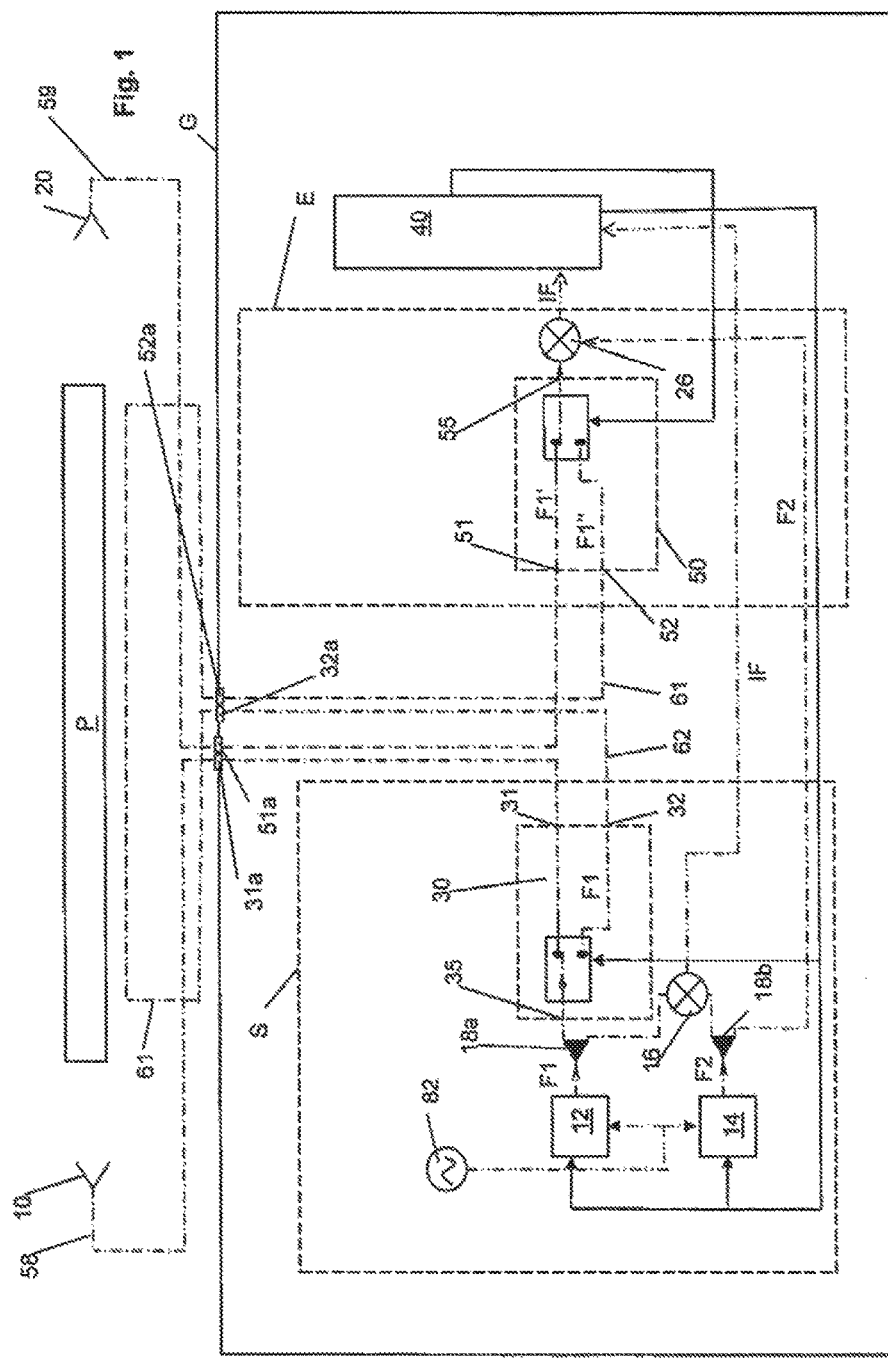
FIG. 1 shows the circuit diagram of an apparatus of a first exemplary embodiment of a first embodiment of the invention.

The following definitions and conventions apply to the following:

A "high-frequency signal" or "microwave" is electromagnetic waves that propagate in a conductor or freely, and have a frequency between 800 MHz and 30 GHz. High frequency signal lines (microwave lines) suitable for such frequencies are known in engineering. The portions of a high-frequency signal line extending between housing and an antenna (HF coupling and HF decoupling units) are formed as coaxial cables and are referred to as HF cables. In the figures, the high-frequency signal lines are shown in dash-dotted form.

By "low frequency" here, one means all electromagnetic waves or signals with a frequency below 200 MHz. Signal lines for transmitting of such low-frequency signals are referred to herein as low-frequency signal lines and are shown in the drawings as solid lines (control and bus lines) or with the pattern dash-dot-dot-dash.

Not all signal lines (whether high frequency signal lines or low frequency signal-lines) have been given their own name/reference in the description and in the drawings for the sake of clarity.

At least outside the housing, the high-frequency signal lines are usually formed as coaxial cables. The low-frequency lines can be realised with coaxial cables as well as with other cables. For cost reasons, higher quality coaxial cables are typically used for the high-frequency signal lines than for the low-frequency signal lines; however, this is not mandatory, it would also be possible, e.g. to use sufficiently high-quality coaxial cables for all signal lines. In this respect, the terms "high-frequency signal line", "HF cable" and "low-frequency signal line" are primarily functional.

Figure 7:
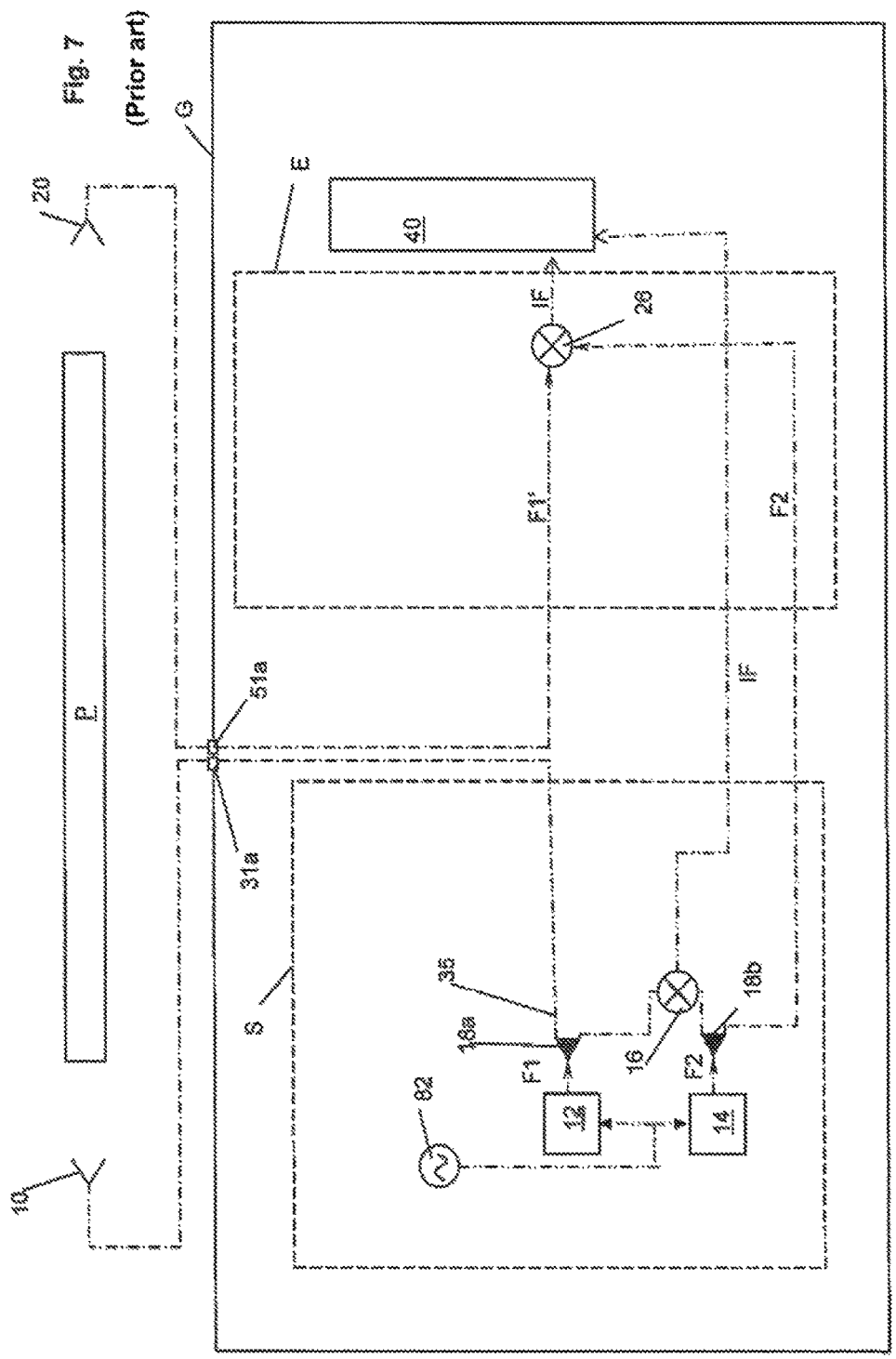
FIG. 7 shows a circuit diagram of an apparatus according to the state of the art.
Figure 8:
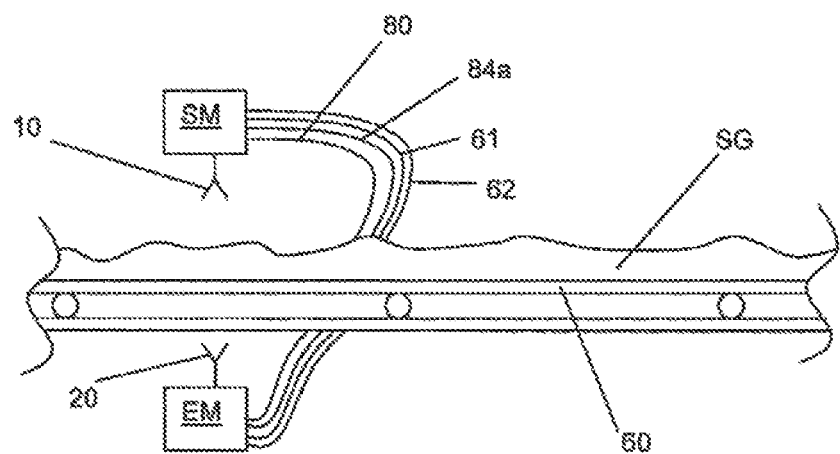
FIG. 8 shows a first preferred application of the invention and FIG. 9 shows a second preferred application of the invention.
Figure 9:
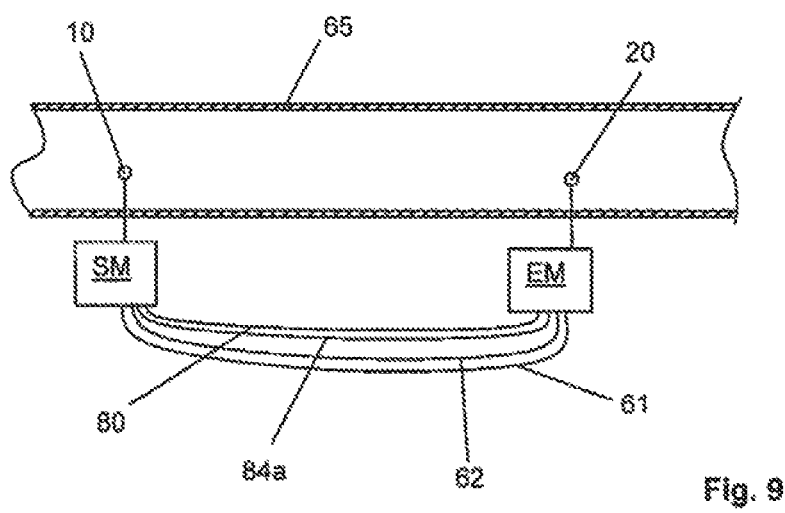

For better understanding, with reference to FIG. 7, reference is first made to the state of the art. FIG. 7 shows a classical heterodyne apparatus in which the measuring device consisting of the transmitting module SM and the receiving module EM is enclosed in a common metal housing G (usually of aluminium).

The transmitting module SM comprises two transmitting-side synthesis generators 12 and 14, two power dividers 18a, 18b, a transmitting-side mixer 16 and a frequency standard 82. The receiving module EM comprises only one receiver-side mixer 26. The evaluation unit consists of a first microcontroller 40 (in the shown exemplary embodiment of the only microcontroller). Transmitting module SM and receiving module EM are connected to each other by means of a high-frequency reference line (F2). The transmitting module SM and the receiving module EM are connected to the evaluation unit (that is, to say, to the first microcontroller) in each case by means of a low-frequency signal line (IF1, IF2). Furthermore, the transmitting module SM is connected by means of a transmitting-side HF connecting cable 58 to a HF coupling unit 10 (hereinafter usually referred to as transmitting antenna), the receiving module EM by means of a receiving-side HF connecting cable 59 with a HF decoupling unit 20 (hereinafter usually referred to as receiving antenna); the housing comprises a first HF signal output 31a and a first HF signal input 51a for this purpose. Transmitting antenna 10 and receiving antenna 20 define a measuring section in which a sample can be arranged. The operation is as follows:

The frequency standard clocks the two transmitting-side synthesis generators 12, 14, wherein the clock frequency may be 10 MHz for example. The first transmitting-side synthesis generator 12 generates a first high-frequency signal F1 having a first high frequency, for example, of 3 GHz, and the second transmitting-side synthesis generator 14 generates a second high-frequency signal F2 having a slightly different high frequency, for example, of 3.001 GHz. The first high-frequency signal F1 of the first transmitting-side synthesis generator 12 is supplied to a first power divider 18a, whose first output is connected to the transmitting antenna 10 and whose second output is connected to the transmitting-side mixer 26. The second transmitting-side synthesis generator 14 is connected to the second power divider 18b, the outputs of which are connected to the transmitting-side mixer 16 and to the receiving-side mixer 26 via the high-frequency reference line 50. The second input of the receiving-side mixer 22 is connected to the receiving antenna 20.

Thus, the transmitting-side mixer 16 generates a first intermediate frequency signal IF1 having a first intermediate frequency that is the difference between the first high frequency (thus, the frequency of the transmitted microwave) and the second high frequency, thus 1 MHz in the selected exemplary embodiment. The receiving-side mixer 26 in turn generates a second intermediate frequency signal IF2 that is the difference of the received microwave (this signal is referred to hereinafter as F1') and the second high frequency signal of the second transmitting-side synthesis generator 14. The frequency of F1 and F1' is the same here, since the transmitting through the sample P changes phase and amplitude, but not the frequency. For this reason, the two intermediate frequency signals IF1 and IF2 also have the same frequency, namely 1 MHz. From the comparison of the first intermediate frequency signal IF1 with the second intermediate frequency signal IF2, both the phase shift and the attenuation experienced by the microwave radiated from the transmitting antenna 10 when the sample P is irradiated can be derived in a known manner, from which again the dielectric properties of the sample can be derived. The corresponding calculations are carried out by the evaluation unit, namely the first microcontroller 40.

In industrial applications, the transmitting-side HF connecting cable 58 and/or the receiving-side HF connecting cable 59 may be relatively long and unprotected, so that their temperature (for example, due to solar radiation) may change relatively rapidly over time. However, this leads to a change in the wave propagation speed that in turn leads to a phase shift, which then leads to a measurement error if countermeasures are not taken.

FIG. 1 shows a first exemplary embodiment of a first embodiment of an apparatus with which the error just described is corrected. The basic structure of this apparatus is identical to the one just described, wherein the following elements are provided additionally.

Connected downstream of the first power divider 18a is a HF splitting device 30 (changeover switch), whose first output 31 is connected to the first HF signal output 31a and whose second output 32 is connected to a second HF signal output 32a of the housing. Similarly, the receiving-side mixer 26 is preceded by an HF merging unit 50 that can be switched, the first input 51 is connected to the first HF signal input 51 and the second input 52 is connected to a second HF signal input 52a of the housing. A first HF bypass cable 61 extends between the second HF signal output 32a and the second HF signal input 52a. Therefore, using the HF splitting device 30 and the HF merging unit 50 it can be switched such that the first high-frequency signal F1 either circumvents the HF connecting cable 58, 59 and the measuring section defined by the antennas 10, 20 and thus becomes the high-frequency signal F', or that it passes through the first HF bypass cable 61 and thus becomes the high-frequency signal F'''. HF splitting device 30 and HF merging unit 50 are driven by microcontroller 40.

This first HF bypass cable 61 (in this exemplary embodiment the only HF bypass cable) preferably comprises the following properties: it has the same electrical and thermal properties as the transmitting-side HF connecting cable 58 and the receiving-side HF connecting cable 59 (i.e., all three cables are identical), having a length equal to the sum of the lengths of the transmitting-side HF connecting cable 58 and the receiving-side HF connecting cable 59 and it is laid so that it has the same temperature as the two HF connecting cables 58, 59. The last-mentioned feature can be achieved, for example, by routing the HF bypass cable in sections parallel to these cables.

When the apparatus is first calibrated, switch over is made to the HF bypass cable 61 in addition to the usual calibration, so that the signal F''' arrives at the receiving-side mixer 26, which mixes the receiving-side mixer 26 with the second high-frequency signal F2. The phase shift between the thus generated second intermediate frequency signal IF2 and the first intermediate frequency signal IF1 is stored as a reference value (reference attenuation and phase shift).

During normal operation (i.e. during the measurement on a sample located in the measuring section), the microcontroller 40 periodically switches over from the measuring section to the HF bypass cable. If a change in the phase shift results between the currently measured phase shift between the second intermediate frequency signal IF2 and the first intermediate frequency signal IF1 and the stored reference phase shift, this indicates a phase shift in the signal F1" and thus a change in temperature in the HF bypass cable 58 assuming that the electronics of the transmitting and receiving modules are stable and works free of drift.

In a symmetrical arrangement, owing to the above-described characteristics of the HF bypass cable with respect to the connecting cables 58, 59, it follows that the signal F1' comprises the same phase shift due to the temperature change of the HF connecting cables 58, 59. In the case of asymmetrical cable length, the change in the electrical properties of the cables can be calculated and correspondingly transferred by calculation to the antenna cables 58 and 59. Without correction, the evaluation unit (in this case the first microcontroller 40) would "offset" this phase shift of the sample, which would lead to a corresponding measurement error. Due to the bypass measurement, the purely temperature-based phase shift is known, however, so that the microcontroller can perform a corresponding correction in the simplest mathematical case by subtracting the temperature-induced phase shift measured at the HF bypass cable from the phase shift measured in the measurement section.

Figure 2:
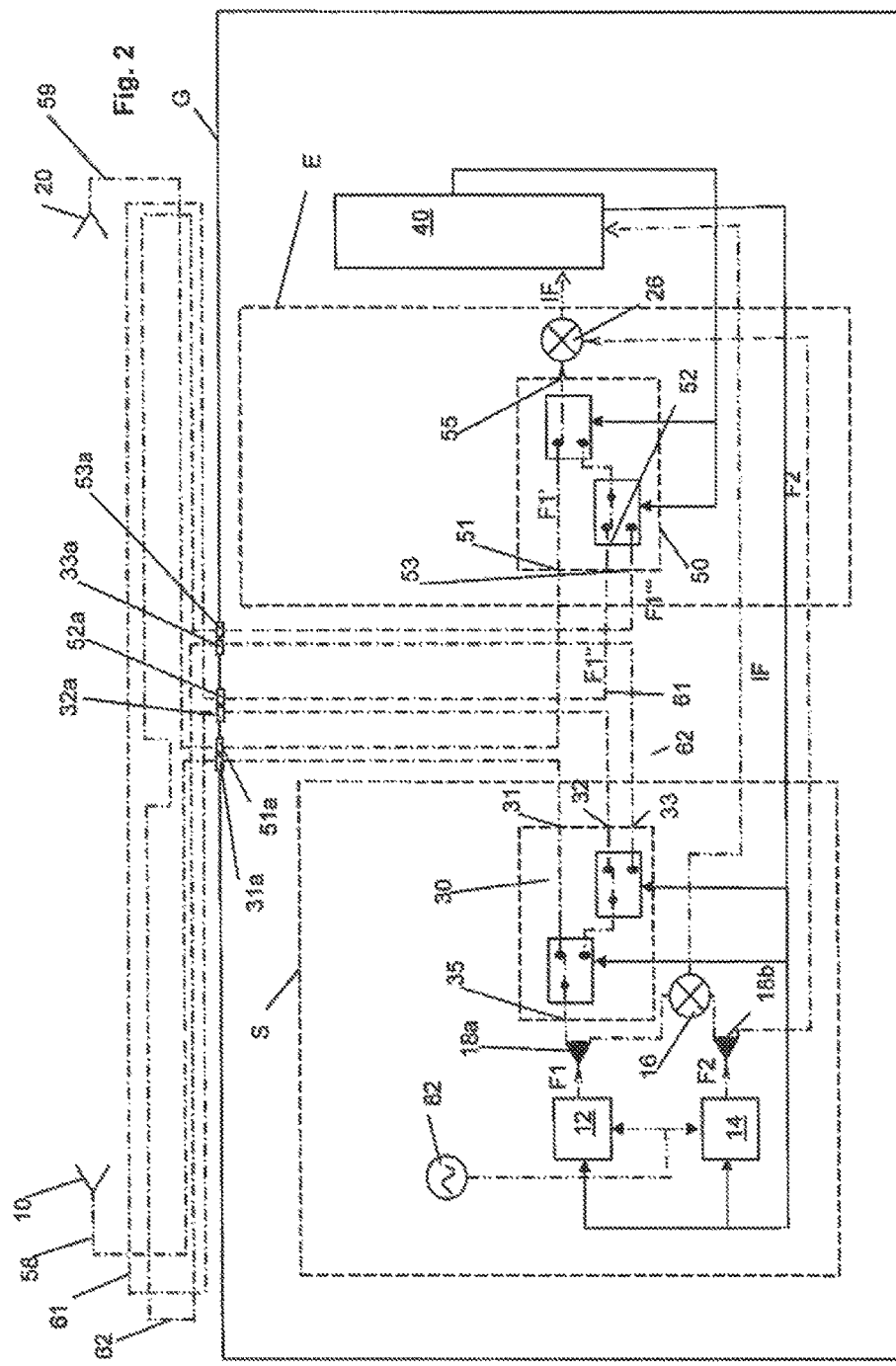
FIG. 2 is a circuit diagram of an apparatus of a second exemplary embodiment of the first embodiment of the invention.

FIG. 2 shows a second exemplary embodiment that is very similar to the first exemplary embodiment. The difference is that two HF bypass cables are provided, namely the first HF bypass cable 61 and the second HF bypass cable 62. Again, all cables 58, 59, 61, 62 extending outside the housing are preferably identical. The first HF bypass cable 61 also here can have a length that corresponds to the sum of the lengths of the two connecting cables. The second HF bypass cable must have a length different from the length of the first HF bypass cable. In order to be able to connect two HF bypass cables, a third HF signal output 33a and a third HF signal input are additionally provided. The HF splitting device 30 accordingly comprises three outputs 31, 32, 33, and the HF merging unit 50 accordingly comprises three inputs 51, 52, 53. All cables can be laid very close to each other, since they are never operated at the same time and are extremely decoupled via the switch, so there is no danger of cross-talkers (this also applies to the first exemplary embodiment).

When calibrating the apparatus, one now obtains two reference phase shifts with respect to IF1, namely the first reference phase shift obtained by mixing F1" (first HF bypass cable) with F2 and the second reference phase shift obtained by mixing F1"' (second HF bypass cable) with F2. During measurement operation, of course, a first phase difference and a second phase difference (in each case based on IF1) are also obtained, so that the evaluation unit can compensate for drift errors of the electronics (transmitting module and receiving module) in addition to the temperature compensation, as shown in the following consideration:

Due to the longer length of the second HF bypass cable, the second phase shift is greater than the first phase shift, and as the temperature of the cable increases, the electrical length changes. If one notes (that is to say the evaluation unit) that first and second phase shifts have changed with the same amount with respect to their respective reference phase shift, then this cannot be due to a temperature change of the cables, but is due to a phase shift that occurs in a drift of electronics. This phase error can then also be taken into account in the correction of phase shift when measuring on the sample.

Mathematically, generally said, one has a system comprising two independent sources of error (temperature change of the cables and electronics drift) and one takes two measurements, wherein the HF cables have the same temperature coefficient so that the size of both errors can be determined.

The presence of a bypass offers a further advantage: One can use the bypass as an empty measurement. Since the electrical length of the bypass is not adjusted to the electrical length of the measuring section, however, an offset will result for both the attenuation D in dB and for the phase shift Phi in GHz, which must be taken into account during the calibration.

Starting from the calibration equation in the simplest form $$W = A*Phi/m'' + B*D/m'' + E$$

Now be taking account of the offset $D_o$ and $Phi_o$ for D or Phi:

$$W = A*(Phi + Phi_o)/m'' + B*(D + D_o)/m'' + E =$$
$$A*(Phi)/m'' + B*(D)/m'' + E$$

with:
W water content
M specific weight of the sample,
A, B, C, coefficients that are determined during the calibration by means of regression.

The second task of the empty measurement is to linearize the frequency response of the measurement with the sample despite none-linear frequency response, e.g. caused by the dispersion of the antennas. Therefore, in addition, a measurement is carried out, which is similar in frequency response to the measurement with the sample, wherein both the frequency response and the mean of the measurement is determined and calculated so that only frequency response affects the measurement, but not the absolute value of the Measurement.

Figure 3:
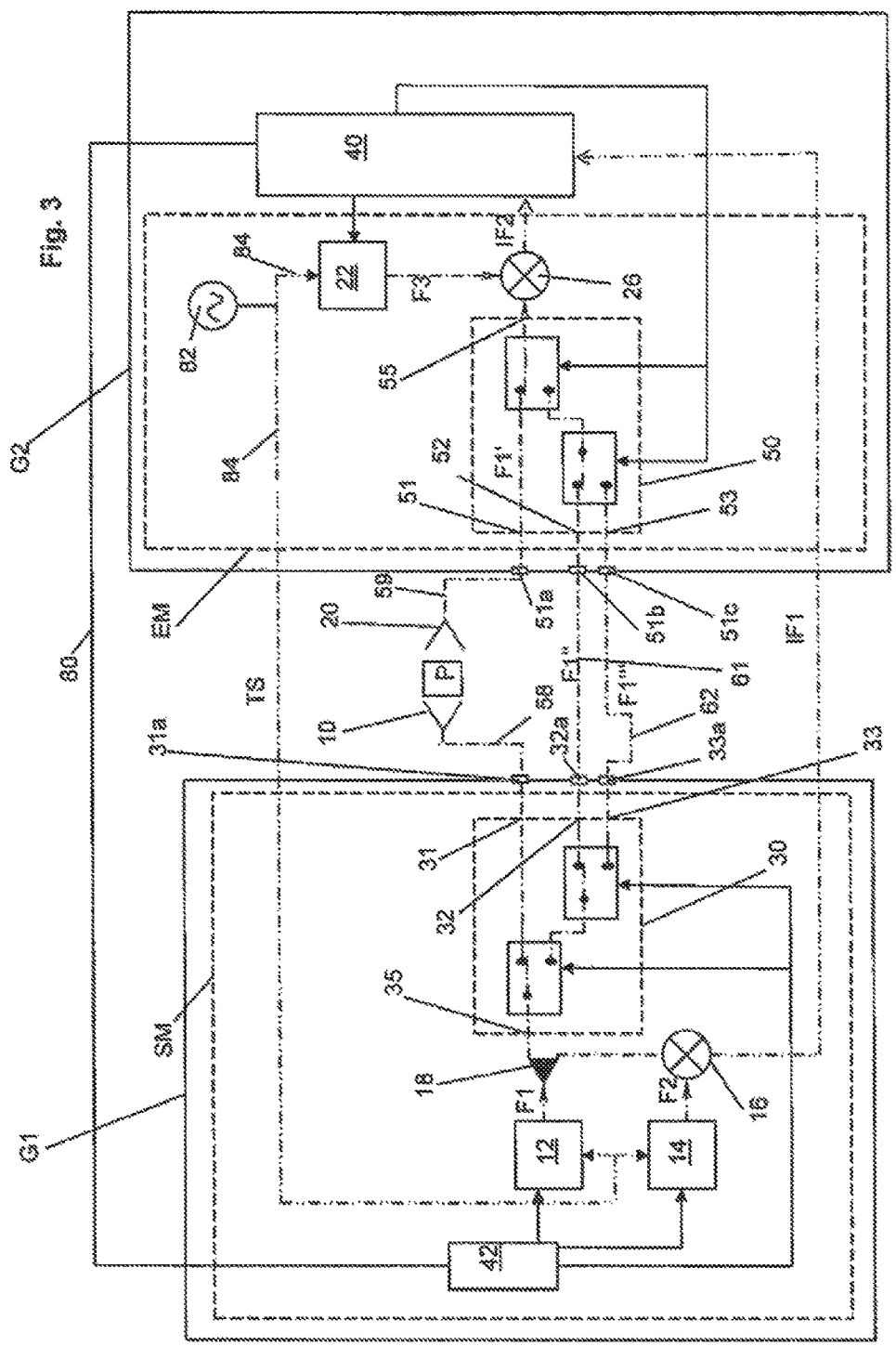
FIG. 3 is a circuit diagram of an apparatus of a first exemplary embodiment of a second embodiment of the invention.

With reference to FIG. 3, a second embodiment of the apparatus according to the invention is now described, which is also designed as a heterodyne system.

The apparatus is designed as disclosed in DE 10 2012 010 255 B3, wherein additionally two HF bypass cables 61, 62 are provided, as described above. Just as in the exemplary embodiment described above, it is possible to switch over between the measuring section and the two HF bypass cables 61, 62, but this achieves a different goal, as is described in more detail later. The two modules SM and EM are spatially separated and housed in separate metal housing G1 and G2. In addition, the evaluation unit in the form of a first microcontroller 40 and a frequency standard 82 is integrated in the second housing G2. However, these components could equally be well housed in the first housing G1 or in a separate housing.

The transmitting module SM comprises two transmitting-side synthesis generators 12 and 14, which respectively generate a high frequency signal F1 and F2, wherein the high frequencies are slightly different from each other, for example, in one state the first high frequency is 3 GHz and the second high frequency is 3.001 GHz. The two transmitting-side synthesis generators 12, 14 are controlled by a second microcontroller 42, which is controlled by the first microcontroller 40. The two microcontrollers 40, 42 are connected by means of a bus line 80. The HF synthesis generators are clocked by a transmitting-side low-frequency synchronisation signal line 34a from the frequency standard 82. The first transmitting-side synthesis generator 12 feeds its high-frequency signal F1 into a power divider 18, which in turn is connected to a transmitting-side mixer 16 and the input 35 of a HF splitting device 30 designed as a switch. As in the previously described exemplary embodiment, the first output 31 of this HF splitting device 30 is connected to the HF coupling unit 10 via a first HF signal output 31a of the housing and the transmitting-side HF connecting cable 58. Again, the HF splitting device 30 comprises two further outputs 32, 33, which are each connected to an HF signal output 32a, 33a of the housing, from each of which an HF bypass signal cable 61, 62 extends. These two HF bypass signal cables 61, 62 also here have the same electrical and thermal properties, but the second HF bypass signal line 62 has a greater length than the first HF bypass signal line 61 (as in the second exemplary embodiment). The HF splitting device 30 is designed in the depicted exemplary embodiment of two switches connected in series, which are controlled by the second microcontroller 42. The second transmitting-side synthesis generator 14 feeds the second high-frequency signal F2 generated by it directly into the transmitting-side mixer 16, which is connected to the evaluation unit, namely to the microprocessor 40 and supplies the first intermediate frequency signal IF1.

The HF decoupling unit 20 is connected via the receiving-side HF connecting cable 59 and the first HF signal input 51a to an input 51 of a HF merging device 50 formed symmetrically to the HF splitting device 30. The two further inputs 52, 53 of the HF merging device 50 are each connected via further HF signal inputs 52a, 53a, each with an HF bypass cable. The HF merging device 50 is controlled via the first microcontroller.

In the receiving module EM, a receiving-side synthesis generator 22 is provided, which in each case generates the same high frequency as the second transmitting-side synthesis generator 14, i.e., 3.001 GHz in the selected exemplary embodiment. This receiving-side synthesis generator 22 is connected to the frequency standard 82 and is controlled by the microcontroller 40. The receiving-side synthesis generator 22 feeds the third high-frequency signal F3 that it generates into the receiving-side mixer 26, the second input of which is connected to the output 55 of the HF merging device 50, so that at the appropriate switching state of HF splitting device 30 and HF merging device 50 it receives the first high-frequency signal F1' transmitted by the sample P.

The transmitting-side mixer 16 generates a first intermediate frequency signal IF1, likewise the receiving-side mixer 26 generates a second intermediate frequency signal IF2, wherein the two intermediate frequencies being equal, namely 1 MHz in the described exemplary embodiment. These intermediate frequency signals are thus low frequency signals (low-frequency signals). These two intermediate frequency signals IF1 and IF2 are fed to the evaluation unit, i.e. the first microprocessor 40. In order to deduce a relevant statement from the phase shift which the first high-frequency signal F1 experiences when passing through the sample P from the phase shift between the first intermediate frequency signal IF1 and the second intermediate frequency signal IF2, all synthesis generators 12, 14 and 22 must be synchronized with one another. This synchronisation is provided by the frequency standard 82, which is connected to the receiving-side synthesis generator 22 by a transmitting-side low-frequency synchronisation signal line 84a and with the two transmitting-side synthesis generators 12, 14 with a receiving-side low-frequency synchronisation signal line 84b and transmits a clock signal TS with which the synthesis generators are coupled in a phase-stable and reproducible manner. The "heart" of such a frequency standard is usually a quartz crystal by which the resonance frequency is used as the standard frequency. Typically, this standard frequency is between 1 and 30 MHz, in particular 10 MHz, as selected in this exemplary embodiment. Both low-frequency synchronisation signal lines 84a, 84b, are low-frequency signal lines, which are preferably physically identical, in particular with the same length (not shown) and formed with identical structure. Due to the local separation of transmitting module SM and receiving module EM, transmitting-side HF connecting cable 58 and receiving-side HF connecting cable 59 can be made very short, so that any temperature fluctuations lead to only small errors. The switchover possibility to the HF bypass cables 61, 62 is used for something else:

As described above, in an initial calibration, reference phase differences between IF1 and the mixture of F1' and F3, between IF1 and the mixture of F1" and F3 and between IF1 and the mixture of F1" and F3 are determined and stored, wherein F2 and F3 are of the same frequency to be used during the measurement operation. This process must be performed for each high-frequency pair that is to be used during a measurement process.

In the measurement state, the input 35 of the HF splitting device is connected to its first output 31 and the first input 51 of the HF merging device 50 is connected to its output 55, so that the apparatus operates as described above and the two HF bypass cables are non-functional (as described above with reference to FIG. 2).

If a frequency change is now carried out by the system (that is to say the transmitting-side synthesis generators 12, 14 are controlled accordingly by the second microcontroller 42 and the receiving-side synthesis generator 22 is controlled accordingly by the first microcontroller 40), the phase position of the receiving-side synthesis generator 22 with respect to the transmitting-side synthesis generators 12, 14 is no longer known because the system does not "know" how the synthesis generators "snap in". Therefore, after a frequency change (for example, from 3.000 GHz and 3.001 GHz to 4.000 GHz and 4.001 GHz), a calibration measurement is first performed by means of the first HF bypass signal line 61, that is, the currently measured phase difference between the mixture F1" and F3 (current IF2) and IF1 is measured. For this purpose, the HF splitting device 30 is switched to the second output 32 and the HF merging device 50 to the second input 52 and a calibration measurement carried out. On the basis of the initial calibration performed, in which a corresponding reference phase shift was measured, the evaluation unit can calculate the phase error that possibly occurred during the frequency change and after switching back to the first output 31 or the first input 51 carry out an appropriate correction when measuring the sample P.

However, in industrial applications where fluctuating temperatures are expected, the electrical properties of the first HF bypass cable 61, which can be relatively long depending on the local conditions, also change with the temperature. In order to be able to compensate for this, the second HF bypass signal line 62 is provided, which, up to the length, has the same properties as the first HF bypass signal line 61. The two HF. Bypass cables 61, 62 are preferably laid parallel to one another, so that they can be assumed to have the same temperature. Thus, a "double calibration measurement" can be carried out at certain time intervals, in which the two HF bypass signal lines are switched in succession between transmitting module SM and receiving module, so that due to different lengths of the two HF bypass signal lines, the temperature effect can be eliminated by calculation, as described above.

Figure 4:
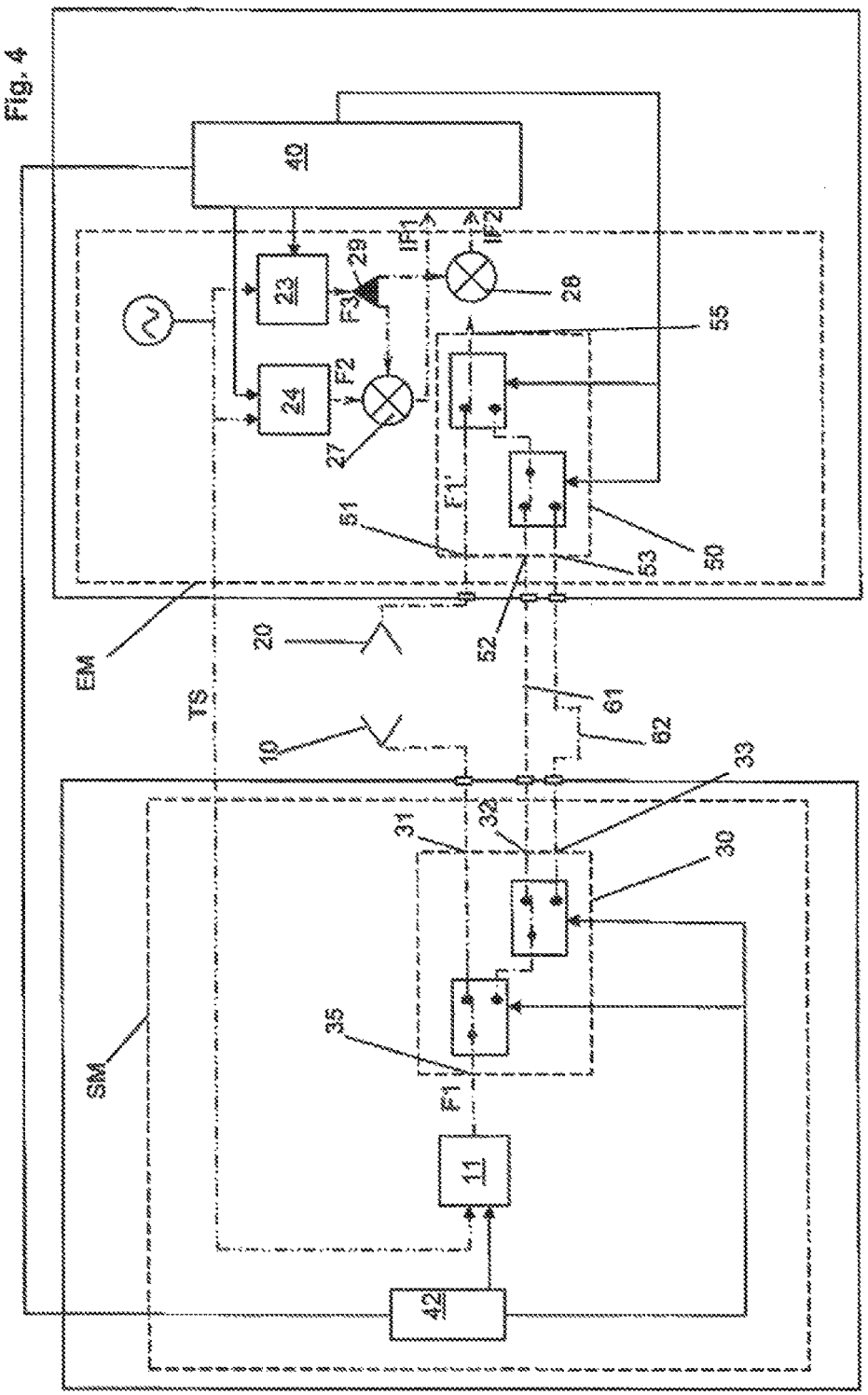
FIG. 4 is a circuit diagram of an apparatus of a second exemplary embodiment of the second embodiment of the invention.

FIG. 4 shows a further exemplary embodiment of the second embodiment. By means of the phase-locked reproducibly coupled synthesis generators, both intermediate frequencies IF1 and IF2 can also be generated on the receiving side, so that the connection cable for the signal of the first intermediate frequency IF1 between the transmitting module SM and the evaluation module AE can be omitted. A concrete exemplary embodiment is shown in FIG. 4: In this case, the transmitting module SM has only one synthesis generator 11. All further components are integrated in the receiving module EM, which thus comprises a first and a second receiving-side synthesis generator 23, 24, wherein the second synthesis generator 24 generates a second high-frequency signal F2 having the same high frequency as the first high-frequency signal F1 of the transmitting-side synthesis generator 11 (for example, again 3 GHz), while the first synthesis generator 23 (as in the exemplary embodiment described above) generates a third high-frequency signal F3 with a slightly different high frequency (for example, again 3.001 GHz). The first intermediate frequency signal IF1 is generated by mixing the second high-frequency signal F2 with the third high-frequency signal F3, for which purpose the first receiving-side mixer 27 is used, whose one input is connected via a power divider 29 to the first receiving-side synthesis generator 23 and whose other input is connected to the second receiving-side synthesis generator 24. The second intermediate frequency signal IF2 is generated as described above, for which the second receiving-side mixer 28 is used, which corresponds to the receiving-side mixer 26 of the first exemplary embodiment. As in the exemplary embodiment described above, all synthesis generators 11, 23, 24 are clocked in phase with the frequency standard 82.

Figure 5:
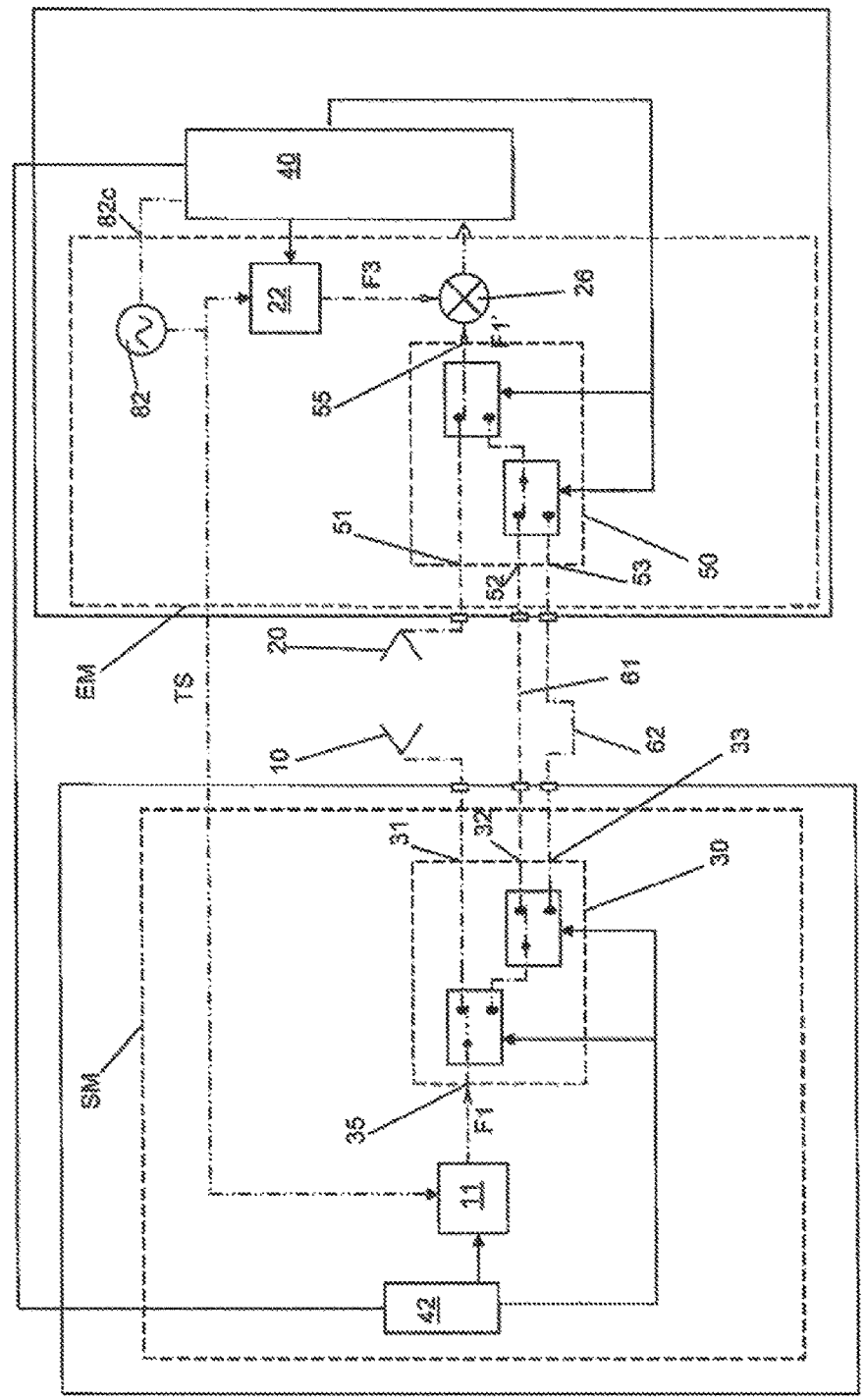
FIG. 5 is a circuit diagram of an apparatus of a third exemplary embodiment of the second embodiment of the invention.

FIG. 5 shows a further exemplary embodiment in which only one transmission-side frequency generator 11 is provided for generating a first high-frequency signal F1 and only one receiving-side frequency generator 22 for generating a further high-frequency signal, which for consistency's sake is referred to here as the third high-frequency signal F3. Here, the clock signal TS of the frequency standard 82 or optionally a signal directly derived from the latter serves as a reference signal (this is the first intermediate frequency signal IF1 in the previous exemplary embodiments). If the clock signal TS is to serve directly as a reference signal, as shown in the exemplary embodiment of FIG. 5 and for which purpose a further low-frequency synchronisation signal line 84c is provided, which connects the frequency standard 82 to the first microprocessor 40, then the frequency of the second intermediate frequency signal IF2 (of the signal mixed from F3 and F1') must be equal to the frequency of the clock signal TS. If the frequency of the clock signal TS is also 10 MHz here, then the frequency of the first high-frequency signal F1 could be 3 GHz and the frequency of the third high-frequency signal F3 could be 3.01 GHz, for instance. This exemplary embodiment leads to a simplification of the circuit, but is still not recommended because by filtering the IF and the frequency standard cannot be separated.

Figure 6:
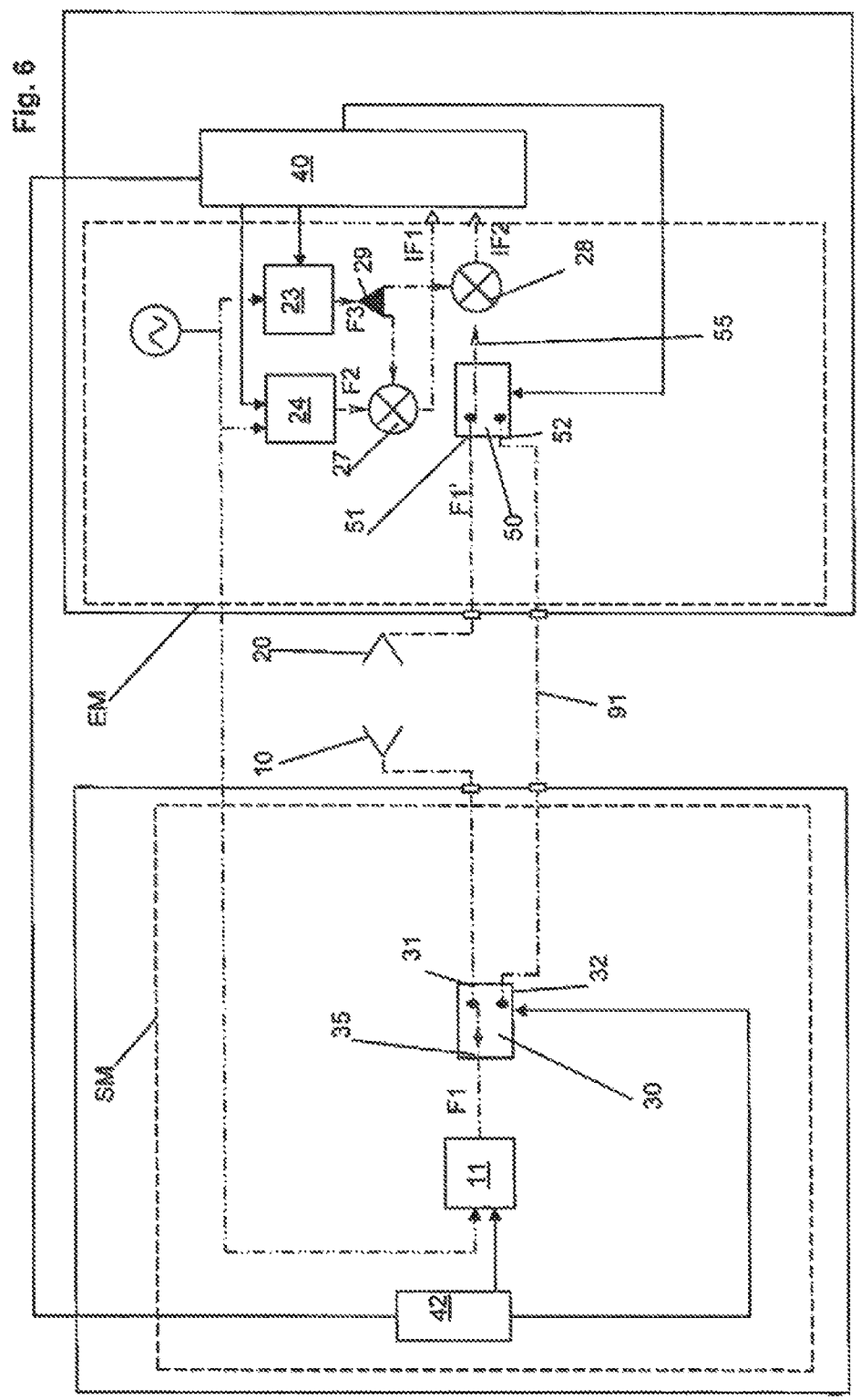
FIG. 6 is a circuit diagram of an apparatus of a fourth-exemplary embodiment of the second embodiment of the invention.

In applications in which fluctuating environmental influences, in particular fluctuating temperatures do not play a decisive role (as in the first exemplary embodiment of the first embodiment) the second HF bypass cable can be optionally omitted. An exemplary embodiment of this is shown in FIG. 6. The HF splitting device (switch) 30 here comprises only two outputs 31, 32 and the HF merging unit 50 comprises only two inputs 51, 52. The only HF bypass cable 61, which can be switched in parallel to the measuring section can be used in this case as described above (i.e. to correct any latching error), but not for temperature compensation.

As already mentioned, the advantages of the improvement according to the invention are particularly evident in the industrial use of such an apparatus, for example in the online measurement of bulk materials SG conveyed on a conveyor 60 such as coal or ore (FIG. 6) or for online measurement of liquid (FIG. 7) flowing through a pipe (65). In addition, the measurement in a container is possible. Shown here are measuring apparatus according to the first two exemplary embodiments.

LIST OF REFERENCE NUMBERS

10 HF coupling unit
11 transmitting-side synthesis generator
12 first transmitting-side synthesis generator
14 second transmitting-side synthesis generator
16 transmitting-side mixer
18 power divider
18a first power divider
18b second power divider
20 HF decoupling unit
22 receiving-side synthesis generator
23 first receiving-side synthesis generator
24 second receiving-side synthesis generator
26 receiving-side mixer
27 first receiving-side mixer
28 second receiving-side mixer
29 power divider
30 HF splitting device
31 first output of the HF splitting device
31a first HF signal output
32 second output of the HF splitting device
32a second HF signal output
33 third output of the HF splitting device
33a third HF signal output
35 input
40 first microcontroller
42 second microcontroller
50 HF merging unit
51 first input
51a first HF signal input
52 second input
52a second HF signal input
53 third input
53a third HF signal input
55 output
58 transmitting side HF connecting cable
59 receiving side HF connection cable
61 first HF bypass cable
62 second HF bypass cable
80 bus
82 frequency standard
90 conveyor belt
95 pipe
F1 first high-frequency signal with first frequency
F2 second high frequency signal with second frequency
F3 third high frequency signal with third frequency
IF1 first intermediate frequency signal with first intermediate frequency
IF2 second intermediate frequency signal with second intermediate frequency
TS clock signal
SM transmitting module
EM receiving module G common housing
G1 first housing (transmitting-side housing)
G2 second housing (receiving-side housing)
SG bulk material

The invention claimed is:

1. A measuring device for the dielectric and/or magnetic properties of a sample by means of a microwave transmission measurement, comprising:
a transmitting module with a first synthesis generator for generating a first high-frequency signal having a first frequency, and a first high frequency (HF) signal output connectible to the first synthesis generator which can be coupled to a HF coupling unit by means of a transmitting-side HF connecting cable;
a receiving module, with a first HF signal input that can be coupled to an HF decoupling unit by means of a receiving side HF connecting cable, and a HF mixer with a first mixer input connectible to the first HF signal input, a second mixer input connected or connectible to the first HF synthesis generator in a homodyne system or a second HF synthesis generator in a heterodyne system, and a mixer output, which outputs an low frequency (LF) signal that is mixed from the two HF signals fed to the inputs,
wherein transmitting module and receiving module are arranged either in a common housing or in separate housings; and
an evaluation unit, which is connected to the output of the mixer and thus processes the LF signal in a first operating state of the apparatus in a first state,
wherein the transmitting module additionally comprises at least one second HF signal output connectible to the first synthesis generator and the receiving module additionally comprises at least one second HF signal input connectible to the first input of the mixer, and
wherein at least one first HF bypass cable, extending outside the housing/the housings, can be connected, whose input can be coupled in the signal path between the first HF synthesis generator and the HF coupling unit and whose output can be coupled in the signal path between the HF output unit and mixer, so that when the first HF bypass cable is coupled, the HF signal from the measuring section, which is defined by the HF decoupling unit and the HF coupling unit when the transmitting-side HF connecting cable and a receiving-side HF connecting cable are coupled, is redirected into the first HF bypass cable, so that the apparatus is then in a second operating state in which the LF signal has a second state in which it contains no information about a sample positioned in the measuring section.

2. The measuring device according to claim 1, wherein:
the transmitting module further comprises a third HF signal output connectible to the first synthesis generator; and
the receiving module further comprises a third HF signal input connectible to the first input of the mixer.

3. The measuring apparatus according to claim 2, wherein:
a first HF switchover or splitting device with an input connected to the first HF synthesis generator, a first output connected to the first HF signal output, a second output connected to the second HF signal output and a third output connected to the third HF signal output is provided; and
a second HF switching unit with a first input connected to the first HF signal input, an output connected to the mixer, a second input connected to the second HF signal input and a third input connected to the third HF signal input is arranged.

4. The measuring device according to claim 1, wherein the first HF synthesis generator is a transmitting-side HF synthesis generator, that the second HF synthesis generator is a receiving-side HF synthesis generator and the HF synthesis generators are each connected by means of a low-frequency synchronisation signal line with a frequency standard and are coupled to this in a phase-locked manner.

5. The measuring device according to claim 4, wherein two transmitting-side HF synthesis generators, and a receiving-side HF synthesis generator or a transmitting side and two receiving-side synthesis generators and a further mixer are provided.

6. The measuring device according to claim 4, wherein at least one receiving-side HF synthesis generator is part of the transmitting module, at least one receiving-side HF synthesis generator is part of the receiving module, the transmitting module and the receiving module are spatially spaced from each other and the at least one HF bypass signal line and the low-frequency synchronisation signal line extend between the transmitting module and the receiving module.

7. The measuring device according to claim 5, wherein the transmitting module is housed in first housing and the receiving module is housed separately in a second housing.

8. The measuring device according to claim 1, wherein the transmitting module and the receiving module are housed in a common housing.

9. The measuring device according to claim 1, wherein the HF signal outputs and the HF signal inputs are accommodated in each case within housing walls.

10. An apparatus for measuring the dielectric and/or magnetic properties of a sample by means of a microwave transmission measurement, comprising:
a measuring device comprising:
a transmitting module with a first synthesis generator for generating a first high-frequency signal having a first frequency, and a first high frequency (HF) signal output connectible to the first synthesis generator which can be coupled to a HF coupling unit by means of a transmitting-side HF connecting cable;
a receiving module, with a first HF signal input that can be coupled to an HF decoupling unit by means of a receiving side HF connecting cable, and a HF mixer with a first mixer input connectible to the first HF signal input, a second mixer input connected or connectible to the first HF synthesis generator in a homodyne system or a second HF synthesis generator in a heterodyne system, and a mixer output, which outputs an low frequency (LF) signal that is mixed from the two HF signals fed to the inputs,
wherein transmitting module and receiving module are arranged either in a common housing or in separate housings; and
an evaluation unit, which is connected to the output of the mixer and thus processes the LF signal in a first operating state of the apparatus in a first state,
wherein the transmitting module additionally comprises at least one second HF signal output connectible to the first synthesis generator and the receiving module additionally comprises at least one second HF signal input connectible to the first input of the mixer, and
wherein at least one first HF bypass cable, extending outside the housing/the housings, can be connected, whose input can be coupled in the signal path between the first HF synthesis generator and the HF coupling unit and whose output can be coupled in the signal path between the HF output unit and mixer, so that when the first HF bypass cable is coupled, the HF signal from the measuring section, which is defined by the HF decoupling unit and the HF coupling unit when the transmitting-side HF connecting cable and a receiving-side HF connecting cable are coupled, is redirected into the first HF bypass cable, so that the apparatus is then in a second operating state in which the LF signal has a second state in which it contains no information about a sample positioned in the measuring section;

the HF coupling unit connected to a first HF output by means of the transmitting-side HF connecting cable running outside the housing/the housings;

the HF decoupling unit connected to the first HF output by means of the receiving-side HF connecting cable running outside the single housing/dual the housings; and the first HF bypass cable connected to the at least one second HF signal output and the at least one second HF signal input, running outside the single housing/dual housing.

11. The apparatus according to claim 10, wherein the transmitting-side HF connecting cable, the receiving-side HF connecting cable and the HF bypass cable are identical in design.

12. The apparatus according to claim 11, wherein the sum of the lengths of the transmitting-side HF connecting cable and the receiving-side HF connecting cable correspond to the length of the HF bypass cable.

13. The apparatus according to claim 12, wherein the transmitting module further comprises a third HF signal output connectible to the first synthesis generator; and the receiving module further comprises a third HF signal input connectible to the first input of the mixer, wherein a second HF bypass cable is connected to the third HF signal output and the third HF signal input, wherein the two HF bypass cables are identical in design and wherein the second HF bypass cable has a greater length than the first HF bypass cable.

14. A measuring method for measuring the dielectric and/or magnetic properties of a sample by means of a microwave transmission measurement, comprising:

using a measuring device comprising:
a transmitting module with a first synthesis generator for generating a first high-frequency signal having a first frequency, and a first high frequency (HF) signal output connectible to the first synthesis generator which can be coupled to a HF coupling unit by means of a transmitting-side HF connecting cablel a receiving module, with a first HF signal input that can be coupled to an HF decoupling unit by means of a receiving side HF connecting cable, and a HF mixer with a first mixer input connectible to the first HF signal input, a second mixer input connected or connectible to the first HF synthesis generator in a homodyne system or a second HF synthesis generator in a heterodyne system, and a mixer output, which outputs a low frequency (LF) signal that is mixed from the two HF signals fed to the inputs, wherein transmitting module and receiving module are arranged either in a common housing or in separate housings; and an evaluation unit, which is connected to the output of the mixer and thus processes the LF signal in a first operating state of the apparatus in a first state, wherein the transmitting module additionally comprises at least one second HF signal output connectible to the first synthesis generator and the receiving module additionally comprises at least one second HF signal input connectible to the first input of the mixer, and wherein at least one first HF bypass cable, extending outside the housing/the housings, can be connected, whose input can be coupled in the signal path between the first HF synthesis generator and the HF coupling unit and whose output can be coupled in the signal path between the HF output unit and mixer, so that when the first HF bypass cable is coupled, the HF signal from the measuring section, which is defined by the HF decoupling unit and the HF coupling unit when the transmitting-side HF connecting cable and the receiving-side HF connecting cable are coupled, is redirected into the first HF bypass cable, so that the apparatus is then in a second operating state in which the LF signal has a second state in which it contains no information about a sample positioned in the measuring section, the HF coupling unit connected to the first HF output by means of the transmitting-side HF connecting cable running outside the housing/ the housings;

the HF decoupling unit connected to the first HF output by means of the receiving-side HF connecting cable running outside the single housing/dual the housings; and the first HF bypass cable connected to the at least one second HF signal output and the at least one second HF signal input, running outside the single housing/dual housing; and using at least one HF bypass cable to compensate for temperature errors of the HF connecting cables, and/or drift of electronic components of the transmitting and receiving module and/or performing empty measurements.

15. The measuring device according to claim 2, wherein the first HF synthesis generator is a transmitting-side HF synthesis generator, the second HF synthesis generator is a receiving-side HF synthesis generator and the HF synthesis generators are each connected by means of a low-frequency synchronisation signal line with a frequency standard and are coupled to this in a phase-locked manner.

16. The measuring device according to claim 3, wherein the first HF synthesis generator is a transmitting-side HF synthesis generator, the second HF synthesis generator is a receiving-side HF synthesis generator and the HF synthesis generators are each connected by means of a low-frequency synchronisation signal line with a frequency standard and are coupled to this in a phase-locked manner.

17. The measuring device according to claim 5, wherein at least one receiving-side HF synthesis generator is part of the transmitting module, at least one receiving-side HF synthesis generator is part of the receiving module, the transmitting module and the receiving module are spatially spaced from each other and the at least one HF bypass signal line and the low-frequency synchronisation signal line extend between the transmitting module and the receiving module.

18. The measuring device according to claim 2, wherein transmitting module and receiving module are housed in a common housing.

19. The measuring device according to claim 3, wherein transmitting module and receiving module are housed in a common housing.

20. The measuring device according to claim 4, wherein transmitting module and receiving module are housed in a common housing.

\* \* \* \* \*